US007229631B2

(12) United States Patent
Olijve et al.

(10) Patent No.: US 7,229,631 B2
(45) Date of Patent: *Jun. 12, 2007

(54) PREPARATION OF OIL-IN-WATER EMULSIONS STABILISED WITH RECOMBINANT COLLAGEN-LIKE MATERIAL AND RELATED PRODUCTS

(75) Inventors: Joseph Hubertus Olijve, Kaatsheuvel (NL); Jan Bastiaan Bouwstra, Bilthoven (NL); Frederik Anton Wolf De, Bunnik (NL); Marc Willem Theodoor Werten, Wageningen (NL); Hendrik Wouter Wisselink, Nijmegen (NL); Richéle Deodata Wind, Wijchen (NL); Tanja Jacoba Bosch Van Den, Ede (NL); Yuzo Toda, Goirle (NL)

(73) Assignee: Fuji Photo Manufacturing Europe B.V., Tilburg (NL)

( * ) Notice: Subject to any disclaimer, the term of this patent is extended or adjusted under 35 U.S.C. 154(b) by 460 days.

This patent is subject to a terminal disclaimer.

(21) Appl. No.: 10/672,040

(22) Filed: Sep. 26, 2003

(65) Prior Publication Data

US 2006/0083760 A1 Apr. 20, 2006

Related U.S. Application Data

(62) Division of application No. 09/602,459, filed on Jun. 23, 2000, now Pat. No. 6,645,712.

(30) Foreign Application Priority Data

Jun. 24, 1999 (EP) ................................ 99202047

(51) Int. Cl.
*A61K 9/00* (2006.01)

(52) U.S. Cl. ...................... 424/400; 430/545; 430/543; 430/627; 430/628; 430/631

(58) Field of Classification Search ................ 430/546, 430/543, 627, 628, 631; 424/400
See application file for complete search history.

(56) References Cited

U.S. PATENT DOCUMENTS

| | | | | |
|---|---|---|---|---|
| 4,021,244 | A | | 5/1977 | Nagatomo et al. |
| 4,988,610 | A | | 1/1991 | Pitt et al. |
| 5,496,712 | A | * | 3/1996 | Cappello et al. ........... 435/69.1 |
| 5,589,322 | A | | 12/1996 | Lobo et al. |
| 5,773,249 | A | | 6/1998 | Cappello et al. |
| 5,801,045 | A | * | 9/1998 | Weber et al. ............ 435/252.3 |
| 5,998,120 | A | | 12/1999 | Connelly et al. |
| 6,150,081 | A | * | 11/2000 | Van Heerde et al. ....... 430/569 |

FOREIGN PATENT DOCUMENTS

| | | |
|---|---|---|
| WO | WO 9623866 | 8/1996 |
| WO | WO 9704123 | 2/1997 |

* cited by examiner

*Primary Examiner*—Michael G. Hartley
*Assistant Examiner*—James Rogers
(74) *Attorney, Agent, or Firm*—Kirkpatrick & Lockhart Preston Gates Ellis LLP

(57) ABSTRACT

The invention provides oil-in-water emulsions comprising recombinant collagen-like polymer in an amount sufficient to act as stabiliser of the emulsion. The polymer is especially a polypeptide which is free of helix structure, has an isoelectric point at least 0.5 pH units removed from the pH of the oil-in-water emulsion. Furthermore, amphiphilic recombinant collagen-like polymers are provided for use in oil-in-water emulsions. The amphiphilic polymers are polar at one end as a result of a relative abundance of polar amino acids, and apolar at the other end as a result of a relative abundance of apolar amino acids.

23 Claims, 1 Drawing Sheet

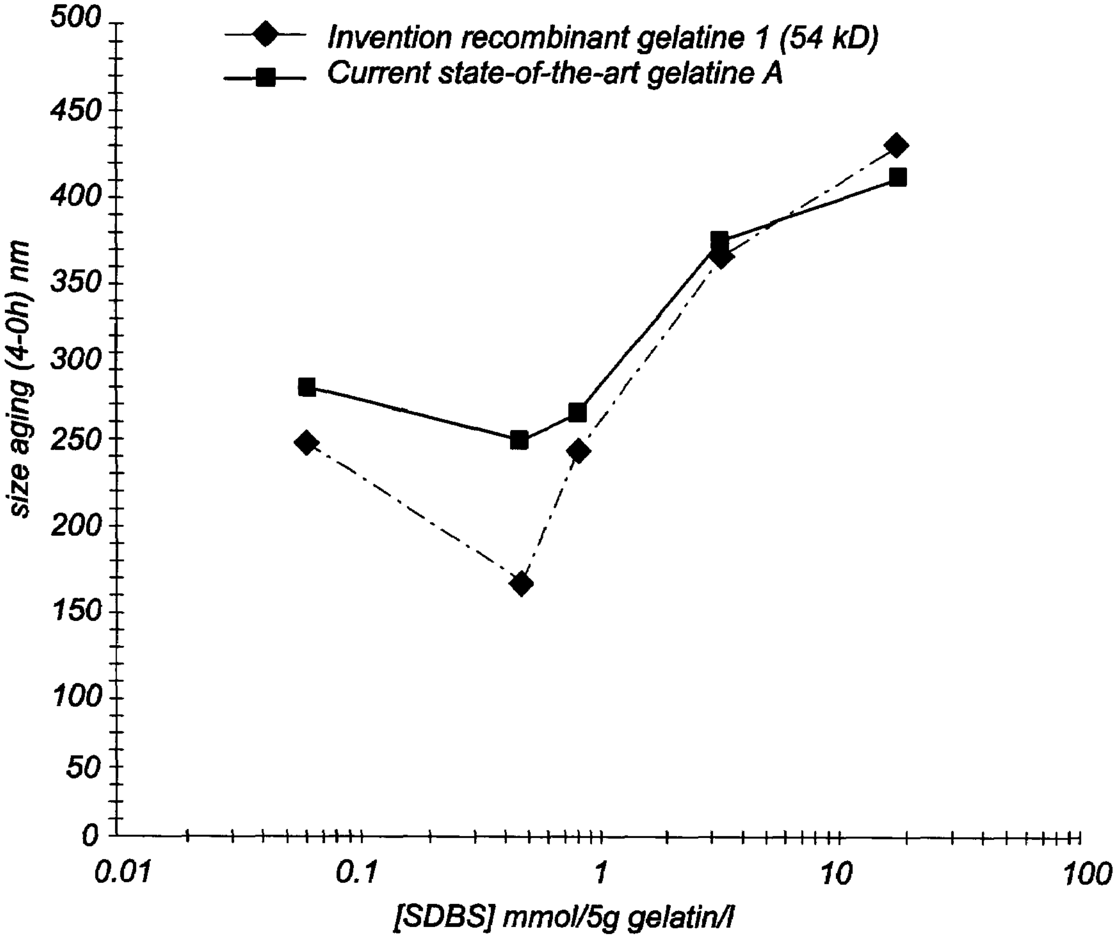
Invention recombinant gelatine 1 (54 kD)
Current state-of-the-art gelatine A
size aging (4-0h) nm
500
450
400
350
300
250
200
150
100
50
0
0.01
0.1
1
10
100
[SDBS] mmol/5g gelatin/l

SEQUENCE LISTING

<160> NUMBER OF SEQ ID NOS: 25

<210> SEQ ID NO 1
<211> LENGTH: 26
<212> TYPE: DNA
<213> ORGANISM: Artificial Sequence
<220> FEATURE:
<223> OTHER INFORMATION: HLP-PA-FW

<400> SEQUENCE: 1
gcgctcgaga aaagagaggc tgaagc 26

<210> SEQ ID NO 2
<211> LENGTH: 108
<212> TYPE: DNA
<213> ORGANISM: Artificial Sequence
<220> FEATURE:
<223> OTHER INFORMATION: OVL-PA-FW

<400> SEQUENCE: 2
gcgctcgaga aaagagaggc tgaagctggt ccacccggtg agccaggtaa cccaggatct 60
cctggtaacc aaggacagcc cggtaacaag ggttctccag gtaatcca 108

<210> SEQ ID NO 3
<211> LENGTH: 110
<212> TYPE: DNA
<213> ORGANISM: Artificial Sequence
<220> FEATURE:
<223> OTHER INFORMATION: OVL-PA-RV

<400> SEQUENCE: 3
tgagaacctt gtggaccgtt ggaacctggc tcaccaggtt gtccgttctg accaggttga 60
ccaggttgac cttcgtttcc tggttgacct ggattacctg gagaaccctt 110

<210> SEQ ID NO 4

-continued

```
<211> LENGTH: 24
<212> TYPE: DNA
<213> ORGANISM: Artificial Sequence
<220> FEATURE:
<223> OTHER INFORMATION: HLP-PA-RV

<400> SEQUENCE: 4

tgagaacctt gtggaccgtt ggaa                                              24


<210> SEQ ID NO 5
<211> LENGTH: 24
<212> TYPE: DNA
<213> ORGANISM: Artificial Sequence
<220> FEATURE:
<223> OTHER INFORMATION: HLP-PB-FW

<400> SEQUENCE: 5

ttccaacggt ccacaaggtt ctca                                              24


<210> SEQ ID NO 6
<211> LENGTH: 115
<212> TYPE: DNA
<213> ORGANISM: Artificial Sequence
<220> FEATURE:
<223> OTHER INFORMATION: OVL-PB-FW

<400> SEQUENCE: 6

ttccaacggt ccacaaggtt ctcagggtaa ccctggaaag aatggtcaac ctggatcccc      60

aggttcacaa ggctctccag gtaaccaagg ttcccctggt cagccaggta accct          115


<210> SEQ ID NO 7
<211> LENGTH: 108
<212> TYPE: DNA
<213> ORGANISM: Artificial Sequence
<220> FEATURE:
<223> OTHER INFORMATION: OVL-PB-RV

<400> SEQUENCE: 7

gcgtctgcag tacgaattct attagccacc ggctggaccc tggtttcctg gtttaccttg      60

ttcacctggt tgaccagggt tacctggctg accaggggaa ccttggtt                  108


<210> SEQ ID NO 8
<211> LENGTH: 26
<212> TYPE: DNA
<213> ORGANISM: Artificial Sequence
<220> FEATURE:
<223> OTHER INFORMATION: HLP-PB-RV

<400> SEQUENCE: 8

gcgtctgcag tacgaattct attagc                                            26


<210> SEQ ID NO 9
<211> LENGTH: 26
<212> TYPE: DNA
<213> ORGANISM: Artificial Sequence
<220> FEATURE:
<223> OTHER INFORMATION: HLP-PA-FW

<400> SEQUENCE: 9

gcgctcgaga aaagagaggc tgaagc                                            26


<210> SEQ ID NO 10
<211> LENGTH: 111
<212> TYPE: DNA
<213> ORGANISM: Artificial Sequence
```

-continued

<220> FEATURE:
<223> OTHER INFORMATION: OVL-NA-FW

<400> SEQUENCE: 10
gcgctcgaga aaagagaggc tgaagctggt ccacccggtg ttccaggttt cattggattc 60
cctggtttgc caggatggcc aggtgtcttc ggtattcctg gttacccagg t 111

<210> SEQ ID NO 11
<211> LENGTH: 114
<212> TYPE: DNA
<213> ORGANISM: Artificial Sequence
<220> FEATURE:
<223> OTHER INFORMATION: OVL-N1A-RV

<400> SEQUENCE: 11
tggccaacct ggaaaaccag gccatcctgg gtaaccagga taaccgaaga tacctgggaa 60
acctggccaa ccaggccagc caaggtaacc tgggtaacca ggaataccga agac 114

<210> SEQ ID NO 12
<211> LENGTH: 25
<212> TYPE: DNA
<213> ORGANISM: Artificial Sequence
<220> FEATURE:
<223> OTHER INFORMATION: HLP-N1A-RV

<400> SEQUENCE: 12
tggccaacct ggaaaaccag gccat 25

<210> SEQ ID NO 13
<211> LENGTH: 25
<212> TYPE: DNA
<213> ORGANISM: Artificial Sequence
<220> FEATURE:
<223> OTHER INFORMATION: HLP-N1B-FW

<400> SEQUENCE: 13
atggcctggt tttccaggtt ggcca 25

<210> SEQ ID NO 14
<211> LENGTH: 107
<212> TYPE: DNA
<213> ORGANISM: Artificial Sequence
<220> FEATURE:
<223> OTHER INFORMATION: OVL-N1B-FW

<400> SEQUENCE: 14
atggcctggt tttccaggtt ggccaggatt cattggtctg cctggttact tgggaccatg 60
gggttttgtt ggttggcctg gttggttggg ttacccaggt ttgttcg 107

<210> SEQ ID NO 15
<211> LENGTH: 108
<212> TYPE: DNA
<213> ORGANISM: Artificial Sequence
<220> FEATURE:
<223> OTHER INFORMATION: OVL-N1B-RV

<400> SEQUENCE: 15
gcgtctgcag tacgaattct attagccacc ggctggaccg tggtcaccgg ggattccctc 60
gtgaccaggg taacctggta atccgaacaa acctgggtaa cccaacca 108

<210> SEQ ID NO 16
<211> LENGTH: 26
<212> TYPE: DNA

-continued

<213> ORGANISM: Artificial Sequence
<220> FEATURE:
<223> OTHER INFORMATION: HLP-PB-RV

<400> SEQUENCE: 16
gcgtctgcag tacgaattct attagc 26

<210> SEQ ID NO 17
<211> LENGTH: 106
<212> TYPE: DNA
<213> ORGANISM: Artificial Sequence
<220> FEATURE:
<223> OTHER INFORMATION: OVL-N2A-RV

<400> SEQUENCE: 17
catagatacc agggtaacca aatggtccca accaaccgaa aggtcctggc caacctggcc 60
aaccaggcca gccaaggtaa cctgggtaac caggaatacc gaagac 106

<210> SEQ ID NO 18
<211> LENGTH: 30
<212> TYPE: DNA
<213> ORGANISM: Artificial Sequence
<220> FEATURE:
<223> OTHER INFORMATION: HLP-N2A-RV

<400> SEQUENCE: 18
catagatacc agggtaacca aatggtccca 30

<210> SEQ ID NO 19
<211> LENGTH: 30
<212> TYPE: DNA
<213> ORGANISM: Artificial Sequence
<220> FEATURE:
<223> OTHER INFORMATION: HLP-N2B-FW

<400> SEQUENCE: 19
tgggaccatt tggttaccct ggtatctatg 30

<210> SEQ ID NO 20
<211> LENGTH: 116
<212> TYPE: DNA
<213> ORGANISM: Artificial Sequence
<220> FEATURE:
<223> OTHER INFORMATION: OVL-N2B-FW

<400> SEQUENCE: 20
tgggaccatt tggttaccct ggtatctatg gttggccagg tttcctgggt taccctggta 60
tcttcggacc atggggtcca tacggtttcc ctggtatgcc aggtatgcct ggtatg 116

<210> SEQ ID NO 21
<211> LENGTH: 117
<212> TYPE: DNA
<213> ORGANISM: Artificial Sequence
<220> FEATURE:
<223> OTHER INFORMATION: OVL-N2B-RV

<400> SEQUENCE: 21
gcgtctgcag tacgaattct attagccacc ggctggacca tcgtgaccgt gatgtccgtg 60
gtgaccgggc ttacccttgt ctcctggcat accaggcata cctggcatac cagggaa 117

<210> SEQ ID NO 22
<211> LENGTH: 599
<212> TYPE: PRT
<213> ORGANISM: Artificial Sequence -continued

```
<220> FEATURE:
<223> OTHER INFORMATION: Protein consisting of two identical nonpolar
      and four polar modules;N1N1P4
<400> SEQUENCE: 22

Gly Pro Pro Gly Val Pro Gly Phe Ile Gly Phe Pro Gly Leu Pro Gly
  1               5                  10                  15

Trp Pro Gly Val Phe Gly Ile Pro Gly Tyr Pro Gly Tyr Leu Gly Trp
             20                  25                  30

Pro Gly Trp Pro Gly Phe Pro Gly Ile Phe Gly Tyr Pro Gly Tyr Pro
         35                  40                  45

Gly Trp Pro Gly Phe Pro Gly Trp Pro Gly Phe Ile Gly Leu Pro Gly
     50                  55                  60

Tyr Leu Gly Pro Trp Gly Phe Val Gly Trp Pro Gly Trp Leu Gly Tyr
 65                  70                  75                  80

Pro Gly Leu Phe Gly Leu Pro Gly Tyr Pro Gly His Glu Gly Ile Pro
                 85                  90                  95

Gly Asp His Gly Pro Ala Gly Val Pro Gly Phe Ile Gly Phe Pro Gly
            100                 105                 110

Leu Pro Gly Trp Pro Gly Val Phe Gly Ile Pro Gly Tyr Pro Gly Tyr
        115                 120                 125

Leu Gly Trp Pro Gly Trp Pro Gly Phe Pro Gly Ile Phe Gly Tyr Pro
    130                 135                 140

Gly Tyr Pro Gly Trp Pro Gly Phe Pro Gly Trp Pro Gly Phe Ile Gly
145                 150                 155                 160

Leu Pro Gly Tyr Leu Gly Pro Trp Gly Phe Val Gly Trp Pro Gly Trp
                165                 170                 175

Leu Gly Tyr Pro Gly Leu Phe Gly Leu Pro Gly Tyr Pro Gly His Glu
            180                 185                 190

Gly Ile Pro Gly Asp His Gly Pro Ala Gly Glu Pro Gly Asn Pro Gly
        195                 200                 205

Ser Pro Gly Asn Gln Gly Gln Pro Gly Asn Lys Gly Ser Pro Gly Asn
    210                 215                 220

Pro Gly Gln Pro Gly Asn Glu Gly Gln Pro Gly Gln Pro Gly Gln Asn
225                 230                 235                 240

Gly Gln Pro Gly Glu Pro Gly Ser Asn Gly Pro Gln Gly Ser Gln Gly
                245                 250                 255

Asn Pro Gly Lys Asn Gly Gln Pro Gly Ser Pro Gly Ser Gln Gly Ser
            260                 265                 270

Pro Gly Asn Gln Gly Ser Pro Gly Gln Pro Gly Asn Pro Gly Gln Pro
        275                 280                 285

Gly Glu Gln Gly Lys Pro Gly Asn Gln Gly Pro Ala Gly Glu Pro Gly
    290                 295                 300

Asn Pro Gly Ser Pro Gly Asn Gln Gly Gln Pro Gly Asn Lys Gly Ser
305                 310                 315                 320

Pro Gly Asn Pro Gly Gln Pro Gly Asn Glu Gly Gln Pro Gly Gln Pro
                325                 330                 335

Gly Gln Asn Gly Gln Pro Gly Glu Pro Gly Ser Asn Gly Pro Gln Gly
            340                 345                 350

Ser Gln Gly Asn Pro Gly Lys Asn Gly Gln Pro Gly Ser Pro Gly Ser
        355                 360                 365

Gln Gly Ser Pro Gly Asn Gln Gly Ser Pro Gly Gln Pro Gly Asn Pro
    370                 375                 380

Gly Gln Pro Gly Glu Gln Gly Lys Pro Gly Asn Gln Gly Pro Ala Gly
385                 390                 395                 400
```

-continued

```
Glu Pro Gly Asn Pro Gly Ser Pro Gly Asn Gln Gly Gln Pro Gly Asn
                405                 410                 415

Lys Gly Ser Pro Gly Asn Pro Gly Gln Pro Gly Asn Glu Gly Gln Pro
            420                 425                 430

Gly Gln Pro Gly Gln Asn Gly Gln Pro Gly Glu Pro Gly Ser Asn Gly
        435                 440                 445

Pro Gln Gly Ser Gln Gly Asn Pro Gly Lys Asn Gly Gln Pro Gly Ser
    450                 455                 460

Pro Gly Ser Gln Gly Ser Pro Gly Asn Gln Gly Ser Pro Gly Gln Pro
465                 470                 475                 480

Gly Asn Pro Gly Gln Pro Gly Glu Gln Gly Lys Pro Gly Asn Gln Gly
                485                 490                 495

Pro Ala Gly Glu Pro Gly Asn Pro Gly Ser Pro Gly Asn Gln Gly Gln
            500                 505                 510

Pro Gly Asn Lys Gly Ser Pro Gly Asn Pro Gly Gln Pro Gly Asn Glu
        515                 520                 525

Gly Gln Pro Gly Gln Pro Gly Gln Asn Gly Gln Pro Gly Glu Pro Gly
    530                 535                 540

Ser Asn Gly Pro Gln Gly Ser Gln Gly Asn Pro Gly Lys Asn Gly Gln
545                 550                 555                 560

Pro Gly Ser Pro Gly Ser Gln Gly Ser Pro Gly Asn Gln Gly Ser Pro
                565                 570                 575

Gly Gln Pro Gly Asn Pro Gly Gln Pro Gly Glu Gln Gly Lys Pro Gly
            580                 585                 590

Asn Gln Gly Pro Ala Gly Gly
        595
```

<210> SEQ ID NO 23
<211> LENGTH: 599
<212> TYPE: PRT
<213> ORGANISM: Artificial Sequence
<220> FEATURE:
<223> OTHER INFORMATION: Protein consisting of two different nonpolar and four polar modules; N1N2P4

<400> SEQUENCE: 23

```
Gly Pro Pro Gly Val Pro Gly Phe Ile Gly Phe Pro Gly Leu Pro Gly
  1               5                  10                  15

Trp Pro Gly Val Phe Gly Ile Pro Gly Tyr Pro Gly Tyr Leu Gly Trp
             20                  25                  30

Pro Gly Trp Pro Gly Phe Pro Gly Ile Phe Gly Tyr Pro Gly Tyr Pro
         35                  40                  45

Gly Trp Pro Gly Phe Pro Gly Trp Pro Gly Phe Ile Gly Leu Pro Gly
     50                  55                  60

Tyr Leu Gly Pro Trp Gly Phe Val Gly Trp Pro Gly Trp Leu Gly Tyr
 65                  70                  75                  80

Pro Gly Leu Phe Gly Leu Pro Gly Tyr Pro Gly His Glu Gly Ile Pro
                 85                  90                  95

Gly Asp His Gly Pro Ala Gly Val Pro Gly Phe Ile Gly Phe Pro Gly
            100                 105                 110

Leu Pro Gly Trp Pro Gly Val Phe Gly Ile Pro Gly Tyr Pro Gly Tyr
        115                 120                 125

Leu Gly Trp Pro Gly Trp Pro Gly Trp Pro Gly Pro Phe Gly Trp Leu
    130                 135                 140

Gly Pro Phe Gly Tyr Pro Gly Ile Tyr Gly Trp Pro Gly Phe Leu Gly
```

-continued

```
145                 150                 155                 160

Tyr Pro Gly Ile Phe Gly Pro Trp Gly Pro Tyr Gly Phe Pro Gly Met
                165                 170                 175

Pro Gly Met Pro Gly Met Pro Gly Asp Lys Gly Lys Pro Gly His His
            180                 185                 190

Gly His His Gly His Asp Gly Pro Ala Gly Glu Pro Gly Asn Pro Gly
        195                 200                 205

Ser Pro Gly Asn Gln Gly Gln Pro Gly Asn Lys Gly Ser Pro Gly Asn
    210                 215                 220

Pro Gly Gln Pro Gly Asn Glu Gly Gln Pro Gly Gln Pro Gly Gln Asn
225                 230                 235                 240

Gly Gln Pro Gly Glu Pro Gly Ser Asn Gly Pro Gln Gly Ser Gln Gly
                245                 250                 255

Asn Pro Gly Lys Asn Gly Gln Pro Gly Ser Pro Gly Ser Gln Gly Ser
            260                 265                 270

Pro Gly Asn Gln Gly Ser Pro Gly Gln Pro Gly Asn Pro Gly Gln Pro
        275                 280                 285

Gly Glu Gln Gly Lys Pro Gly Asn Gln Gly Pro Ala Gly Glu Pro Gly
    290                 295                 300

Asn Pro Gly Ser Pro Gly Asn Gln Gly Gln Pro Gly Asn Lys Gly Ser
305                 310                 315                 320

Pro Gly Asn Pro Gly Gln Pro Gly Asn Glu Gly Gln Pro Gly Gln Pro
                325                 330                 335

Gly Gln Asn Gly Gln Pro Gly Glu Pro Gly Ser Asn Gly Pro Gln Gly
            340                 345                 350

Ser Gln Gly Asn Pro Gly Lys Asn Gly Gln Pro Gly Ser Pro Gly Ser
        355                 360                 365

Gln Gly Ser Pro Gly Asn Gln Gly Ser Pro Gly Gln Pro Gly Asn Pro
    370                 375                 380

Gly Gln Pro Gly Glu Gln Gly Lys Pro Gly Asn Gln Gly Pro Ala Gly
385                 390                 395                 400

Glu Pro Gly Asn Pro Gly Ser Pro Gly Asn Gln Gly Gln Pro Gly Asn
                405                 410                 415

Lys Gly Ser Pro Gly Asn Pro Gly Gln Pro Gly Asn Glu Gly Gln Pro
            420                 425                 430

Gly Gln Pro Gly Gln Asn Gly Gln Pro Gly Glu Pro Gly Ser Asn Gly
        435                 440                 445

Pro Gln Gly Ser Gln Gly Asn Pro Gly Lys Asn Gly Gln Pro Gly Ser
    450                 455                 460

Pro Gly Ser Gln Gly Ser Pro Gly Asn Gln Gly Ser Pro Gly Gln Pro
465                 470                 475                 480

Gly Asn Pro Gly Gln Pro Gly Glu Gln Gly Lys Pro Gly Asn Gln Gly
                485                 490                 495

Pro Ala Gly Glu Pro Gly Asn Pro Gly Ser Pro Gly Asn Gln Gly Gln
            500                 505                 510

Pro Gly Asn Lys Gly Ser Pro Gly Asn Pro Gly Gln Pro Gly Asn Glu
        515                 520                 525

Gly Gln Pro Gly Gln Pro Gly Gln Asn Gly Gln Pro Gly Glu Pro Gly
    530                 535                 540

Ser Asn Gly Pro Gln Gly Ser Gln Gly Asn Pro Gly Lys Asn Gly Gln
545                 550                 555                 560

Pro Gly Ser Pro Gly Ser Gln Gly Ser Pro Gly Asn Gln Gly Ser Pro
                565                 570                 575
```

-continued

```
Gly Gln Pro Gly Asn Pro Gly Gln Pro Gly Glu Gln Gly Lys Pro Gly
            580                 585                 590

Asn Gln Gly Pro Ala Gly Gly
        595


<210> SEQ ID NO 24
<211> LENGTH: 21
<212> TYPE: DNA
<213> ORGANISM: Artificial Sequence
<220> FEATURE:
<223> OTHER INFORMATION: PRIMER for PCR

<400> SEQUENCE: 24

gactggttcc aattgacaag c                                              21


<210> SEQ ID NO 25
<211> LENGTH: 21
<212> TYPE: DNA
<213> ORGANISM: Artificial Sequence
<220> FEATURE:
<223> OTHER INFORMATION: PRIMER for PCR

<400> SEQUENCE: 25

gcaaatggca ttctgacatc c                                              21
```

PREPARATION OF OIL-IN-WATER EMULSIONS STABILISED WITH RECOMBINANT COLLAGEN-LIKE MATERIAL AND RELATED PRODUCTS

CROSS-REFERENCE TO A RELATED APPLICATION

This application is a divisional of application Ser. No. 09/602,459 filed Jun. 23, 2000, now U.S. Pat. No. 6,645,712, which latter application claims priority of European Patent Application No. 99 202047 filed Jun. 24, 1999.

SUMMARY OF THE INVENTION

The subject invention is directed at an oil-in-water emulsion in which recombinant collagen-like polymer is applied as a stabiliser. The stabilising effect occurs already at the stage of formation i.e. on the initial size of the droplets in the emulsion. Also the stabilizing effect is visible when assessing the ageing of the oil-in-water emulsion. In both cases the droplet size is significantly reduced vis-à-vis the prior art oil-in-water emulsions comprising gelatin. The stabilising effect occurs at a range of temperatures and a range of pH values. It now in fact has become possible to operate processes requiring oil-in-water emulsions at lower temperatures than was possible to date and also at lower pH values than normally are applied to date. The same holds true for the storage temperature and pH at which the oil-in-water emulsions according to the invention can currently be maintained. The oil-in-water emulsions can now be stored longer than was previously the case. Also the oil-in-water emulsions according to the invention can be as stable as the prior art oil-in-water emulsions comprising gelatin at lower concentrations of surfactant than used in the prior art oil-in-water emulsions.

In addition the subject invention provides the possibility to use recombinant collagen-like polymer which are composed of polar and apolar end tails for oil-in-water emulsions and also provides for the first time the bipolar, or more specifically amphiphilic, compounds as such and a description of a method to achieve the production of such compounds.

FIELD OF THE INVENTION

Oil-in-water emulsions consist of hydrophobic droplets in a hydrophilic continuous phase, The interfacial area between these hydrophobic droplets and the hydrophilic continuous phase is stabilised with surfactants and/or polymers.

In the manufacturing process, the size of the droplets in the oil-in-water emulsion is a factor needing careful control. The average size of the droplets in the oil-in-water emulsion should be small i.e. the initial size of the droplets should be as low as possible. Also the size stability of the droplets after making the oil-in-water emulsion should be high i.e. the ageing stability should be as high as possible thus ensuring the increase in droplet size in time is kept as low as possible. To realise this small initial size and this limited ageing, the oil droplets can be stabilised by gelatin.

Present stabilisation methods however have several disadvantages:

1. The initial size of the oil-in-water emulsion is rather large,
2. The stabilisation capability of the present gelatin is limited, meaning that in the manufacturing process the oil-in-water emulsions have a limited life time in which they can be applied for specific functions.

The presently used polymer-like materials (like gelatin) originate from natural sources and the structure and the related rheological and surface chemical characteristics can be modified only in a limited manner. *J. Colloid Polym. Sci* 272: 433–439 for example reveals experimental data about the relation between the molecular mass distribution of non-recombinant natural gelatin and it's effectiveness in the stabilisation of oil-in-water emulsions. In the case of gelatin samples with a content of more than 30% of the low molecular weight fraction as described in the article an improved stabilisation was obtained in comparison to the native non recombinant non hydrolysed gelatin. The problem still remained with this modified gelatin that the reproducibility of such processes using natural gelatin sources is not extremely good. In particular this is a preferred requirement for photographic applications.

In addition when considering use of oil-in-water emulsions for consumption purposes e.g. in foodstuffs the risk associated with mad cows disease for example can have a prohibitive effect on the use of gelatin derived from natural sources as a stabiliser.

DETAILED DESCRIPTION OF THE INVENTION

The invention is directed at an oil-in-water emulsion comprising recombinant collagen-like (or gelatin-like) polymer in an amount sufficient to act as a stabiliser of the emulsion. The advantages thereof are described in detail elsewhere in the description. An oil-in-water emulsion according to the invention suitably is one wherein the recombinant collagen-like polymer is free of triple helix structure. The recombinant collagen-like polymer is suitably free of any helix structure. It is a preferred embodiment of the invention that the recombinant collagen-like polymer of the oil-in-water emulsion is free of hydroxyproline as this ensures the absence of (triple) helix formation. The triple helical structure is present in natural gelatin. The absence of the (triple) helical structure is advantageous, because the emulsification can be operated at lower temperatures (15–40° C.) than the traditional temperature during the emulsification process T higher than 40° C.).

The method of arriving at recombinant collagen-like polymer has been described in detail in commonly owned U.S. Pat. No. 6,150,081, inventors van Heerde et al., for example at column 14, line 48 to column 15, line 17, at column 22 , line 51 to column 25 line 18 and elsewhere throughout the specification, the entire disclosure of which patent is hereby incorporated herein by reference thereto. The methodology is described in the publication 'High yield secretion of recombinant gelatins by *Pichia pastoris*', M. W. T. Werten et al., *Yeast*, 15, 1087–1096 (1999), in press.

To be defined as collagen-like at least one GXY domain should be present of at least a length of 5 consecutive GXY triplets and at least 20% of the amino acids of the recombinant collagen-like polymer should be present in the form of consecutive GXY triplets, wherein a GXY triplet consists of G representing glycine and X and Y representing any amino acid. Suitably at least 5% of X and/or Y can represent proline and in particular at least 5%, more in particular between 10 and 33% of the amino acids of the GXY part of the recombinant collagen-like polymer is proline. For the purposes of this patent application the recombinant collagen-like polymer consists of at least 4 different amino acids, preferably more than 10 different amino acids, more preferably more than 15 different amino acids. It can comprise any of the amino acids known. A preferred oil-in-water emulsion according to the invention is one, wherein the recombinant collagen-like polymer comprises at least one lysine residue.

Any of the embodiments disclosed in the van Heerde et al. U.S. Pat. No. 6,150.081 can be applied for the oil-in-water emulsions according to the invention. A preferred embodiment of an oil-in-water emulsion according to the invention is one wherein the recombinant collagen-like polymer has an isoelectric point at least 0.5 pH units removed from the pH of the oil-in-water emulsion itself. Suitably one pH unit removed or even more. The advantage hereof is that the pH at which the emulsion needs to be maintained or used or prepared can vary depending on the isoelectric point (pI) of the applied recombinant collagen-like polymer. The recombinant technology enables variation previously unavailable for tailoring the polymer and thus tailoring the pI. It will be appreciated that not all processes requiring an oil-in-water emulsion are best carried out at pH 6 which is the pH value at which prior art gelatin comprising oil-in-water emulsions were optimally used. Naturally the pH=6 can also be used in those cases where it is still useful or in fact optimal. However the oil-in-water emulsions according to the invention no longer need the strict control of the pH during any of the processes e.g. preparation, storage or application as was previously the case. Now it has in addition become possible to use the oil-in-water emulsions according to the invention at pH=5. It has now become possible to develop oil-in-water emulsions with recombinant collagen-like polymers of extremely divergent pI values. Suitable embodiments involve pI anywhere from 4–10. pI equal to or higher than 6, equal to or higher than 7 and even equal to or higher than 8 and higher than 9 have been achieved and they are illustrated in the examples. We also illustrate pI selected from 4–7. The presence of collagen-like polymers with an isoelectric point far from the actual pH of the OW emulsion according to the invention is preferred. Such a pH has the advantage that the overall charge and the overall three dimensional conformation of the polymer is independent of the pH, and so the steric stabiisation of the OW emulsion is also independent of the pH.

An oil-in-water emulsion according to the invention will use recombinant collagen-like polymer with a molecular weight of at least 2.5 kDa. Suitably the molecular weight is lower than 170 kDa, preferably lower than 100 kDa. We have found improved results when the molecular weight is higher than 20 kDa, preferably higher than 25 kDa and even more preferably higher than 50 kDa. A preferred range thus goes from 20 kDa to 100 kDa.

An oil-in-water emulsion according to the invention, which is particularly useful, is one, wherein the recombinant collagen-like polymer is present in a homodisperse size distribution, A homodisperse size distribution means that the optimal size distribution and the uniformity and reproducibility can be guaranteed for the desired application. According to the invention, the notion "homodisperse" preferably means that at least 75% of the molecules have a molecular weight between −10% and +10% of the average molecular weight. It is clear for example that steric hindrance is limited in cases where the size is too low. A size that is too high causes a high viscosity, which is inconvenient for the emulsion equipment and for the emulsification process. The invention now provides the opportunity to regulate this in an optimal manner. A lower viscosity enables application of higher concentrations of the gelatin and the oil. Thus the ratio of oil versus water can be improved, which will be advantageous for several photographic applications.

In an alternative embodiment an oil-in-water emulsion according to the invention, is one wherein the recombinant collagen-like polymer is present together with non recombinant collagen i.e. an oil-in-water emulsion which comprises a mix with natural gelatin or prior art gelatins can also be used. Surprisingly good results concerning stability vis-à-vis initial size and ageing stability are possible. No phase separation occurs and dissolving occurs only in the water, which is particularly interesting for example in photographic application. In a suitable embodiment the oil-in-water emulsion according to the invention can be one, wherein the recombinant collagen-like polymer is present together with non recombinant collagen in a ratio of 99%–20% on weight basis of recombinant collagen-like polymer on the basis of total weight of collagen-like polymer in the oil-in-water emulsion. The initial size of the oil-in-water emulsion resulting from this mixing process, stabilised by said protein-like material made by genetic engineering, was smaller than the initial size of the oil-in-water stabilised by traditional polymer-like material, and the ageing characteristics of said oil-in-water emulsion were improved, under a wide variety of conditions (variation in T, surfactant, pH, polymer-like stabiliser combinations, etc.), as compared with the prior art.

Of particular interest is the fact that oil-in-water emulsions according to any of the embodiments of the invention exhibit better initial size characteristics as can be determined by measuring the droplet size at a particular pH and temperature of the emulsion and measuring the size under the same conditions for a prior art oil-in-water emulsion. A suitable test revealing better initial size characteristics can comprise measuring a smaller initial droplet size at T=40° C. or less and pH=5 at 2 ml scale using ultrasonic technique in comparison to prior art gelatin under corresponding conditions, e.g. at a temperature T selected from the range of 10–40° C., suitably 15–40° C. e.g. T=30, 25, 20, 15 or 10° C., wherein the comparison is optionally carried out in the presence of surfactant, e.g. in an amount corresponding to 0.4868 mM SDBS/5 grams of collagen-like polymer/liter. An improvement can comprise the oil-in-water emulsion according to the invention exhibiting better initial size characteristics as can be determined by measuring a smaller initial droplet size than 600 nm, preferably below 500 nm, even lower than 350 nm, 250 nm and more preferably below 200 nm at T=40° C. or less e.g. at a T selected from the range of 10–40, suitably 15–40° C. e.g. T=30, 25, 20, 15 or 10° C. at pH=5, wherein the comparison is carried out optionally in the presence of a surfactant, e.g. in an amount corresponding to 0.4868 mM SDBS/5 grams of collagen-like polymer per liter.

Not only is an improvement of initial size often found, but also better ageing characteristics as can be determined by measuring the droplet size after a period of time at a particular pH and temperature of the emulsion and measuring the size under the same conditions for a prior art oil-in-water emulsion. An example of a suitable test to reveal this characteristic is by measuring an increase in droplet size after 4 hours at T=40° C. or less and pH=6 at 2 ml scale using ultrasonic technique in comparison to prior art gelatin under corresponding conditions, e.g. a T from the range 10–40, suitably 15–40° C. e.g. T-30, 25, 20, 15 or 10° C., wherein the comparison is optionally carried out in the presence of surfactant, e.g. in an amount corresponding to 0.4868 mM SDBS/5 grams of collagen-like polymer/liter. Suitably one will find for oil-in-water emulsions according to the invention better ageing characteristics as can be determined by measuring a smaller increase in droplet size after 4 hours than 450 nm, preferably below 400 nm, preferably below 350 nm and more preferably below 300 nm and even below 250 nm at T=40° C. or less e.g. at a T selected from the range of 10–40° C., suitably 15–40° C. e.g. T30, 25, 20, 15 or 10° C. at pH=6, wherein the comparison is carried out optionally in the presence of surfactant, e.g. in an amount corresponding to 0.4868 mM SDBS/5 grams of collagen like polymer/liter.

The tests can be carried out at different pH values depending on the recombinant collagen-like polymer used in the oil-in-water emulsion. The improvement is generally more noticeable at lower temperatures and at pH lower than those generally used for prior art gelatins i.e. at a pH lower than 6 suitably lower than 5.5 e.g. around 5 or lower.

An oil-in-water emulsion according to any of the embodiments of the invention will not exhibit gelation at a temperature below 30° C.

Oil-in-water emulsions according to any of the embodiments of the invention will exhibit increased stability in the presence of surfactant at a concentration below that equivalent to 1 mmol SDBS/5 gram gelatin/l as can be determined by measurement of droplet size increase after 4 hours at pH 6.0 and T=40° C. below 250 nm.

An oil-in-water emulsion according to any of the embodiments of the invention can comprise the recombinant collagen-like polymer in concentrations of collagen-like polymer in the range of 2–100 gram/l solvent, in particular between 5 and 50 g/l solvent. This is advantageous in comparison to the prior art oil-in-water emulsions i.e. higher gelatin concentrations are feasible than oil-in-water emulsions using gelatin applied in the prior art.

An oil-in-water emulsion according to any of the embodiments of the invention can exhibit a viscosity in the range 0.005–8 mPa when dissolved in a concentration of 6.6% in water at a temperature of 40° C.

Due to the development of the recombinant technology it has now become possible to develop for use specifically in oil-in-water emulsion according to any of the embodiments of the emulsions according to the invention recombinant collagen-like polymer exhibiting an amphiphilic structure, with one end of the molecule being polar and the other end being apolar e.g. wherein the recombinant collagen-like polymer exhibits an amphiphilic structure, with one end of the molecule being polar due to the presence of a sufficient number of polar amino acid residues to render that end polar and the other end being apolar due to the presence of a sufficient number of apolar amino acid residues to render that end apolar. Collagen-like polymers with an amphipolar character (one side hydrophilic, one side hydrophobic) show an optimal interfacial behaviour and have a strong preference for a position on the oil-water interface (with one leg in the oil-phase and "one leg" in the water-phase, resulting in a low interfacial tension) by which the initial size and stabiisation are optimised. The manufacture of the polar hydrophilic collagen molecule can be made following the detailed method described in van Heerde et al. U.S. Pat. No. 6,150,081. Obviously the changes required in the amino acid sequence can be achieved in a maimer well known to the skilled person when wishing to introduce a few specific amino acid substitutions. The skilled person also knows which amino acids can be substituted and which amino acids can be used to enhance polarity or apolarity. The polar and apolar constructs can be combined using standard methodologies of ligation for the manufacture of the bi-functional collagen-like polymer. Not only is an oil-in-water emulsion as such part of the invention but also any of the bipolar molecules as such and a process for making them. An amphiphilic recombinant collagen-like polymer i.e. polar at one end and apolar at the other to a degree sufficient for the polar end to extend into a water phase and the apolar end to extend into an oil phase, wherein recombinant collagen-like is further as described for any of the recombinant collagen-like polymers as components of an oil-in-water emulsion according to the invention is thus also covered.

The amphiphilic nature of the preferred collagen-like polymers of the invention can be defined with reference to the transfer free energy of the individual amino acids constituting the polar and apolar parts of the polymer, respectively. This transfer fee energy (ΔF) is the energy (in kcal/mole) of the amino acid residue in an α-helix to be transferred from the membrane interior to the water phase. These energy values as defined by Engelman et al, *Ann. Rev. Biophys. Biophys. Chem.* 15 (1986), 330, are summarised in the table below.

| a.a | Phe | Met | Ile | Leu | Val | Cys | Trp | Ala | Thr | Gly |
|---|---|---|---|---|---|---|---|---|---|---|
| ΔF | 3.7 | 3.4 | 3.1 | 2.8 | 2.6 | 2 | 1.9 | 1.6 | 1.2 | 1.0 |
| a.a. | Ser | Pro | Tyr | His | Gln | Asn | Glu | Lys | Asp | Arg |
| ΔF | 0.6 | −0.2 | −0.7 | −3 | −4.1 | −4.8 | −8.2 | −8.8 | −9.2 | −12.3 |

The polarity of a given amino acid sequence is defined herein as the average transfer free energy per amino acid of the sequence, which equals the sum of the product of the number of individual amino acids and the transfer free energy of each amino acid, divided by the total number of amino acids. In a formula:

$$\text{Polarity}=(\Sigma n_i \cdot \Delta F_i / n_t$$

wherein $n_i$ is the number of each individual amino acid, $\Delta F_i$ is the transfer free energy of the corresponding amino acid, and $n_i$ is the total number of amino acids. As an example, a 15-mer apolar peptide having the following amino acid sequence:

```
Gly Pro Pro Gly Val Pro Gly Phe Ile Gly Phe Pro

Gly Leu Pro
```

has the following amino acid composition: 5 Gly+5 Pro+1 Val+2 Phe+1 Ile+1 Leu, and hence it has the following polarity (in kcal/mole per amino acid):

$$(5*1.0+5*-0.2+1*2.6+2*3.7+1*3.1+1*2.8)/15=19.9/15=+1.33$$

Apolar sequences generally have positive polarity values, whereas polar sequences have negative polarity values. According to the invention, amphiphilic collagen-like polymers have a polar part and an apolar part, the polar part having a polarity value which is at least 0.3 lower (i.e. less positive or more negative), preferably at least 0.5 lower, more preferably at least 0.7 lower than the apolar part. The polar part an the apolar part may be separated by a bridge, the polarity of which may be intermediate. It is preferred that the polar part and apolar part each make up at least 10% of the total length (defined in chain atom numbers) of the polymer, preferably each at least 20% of the length. In particular each part (polar and apolar) contains at least 10, more in particular at least 20, most particularly at least 30 amino acids, up to half of the total number of amino acids. Preferably the polar and apolar parts are located at the two opposite ends of the polymer, with preferably less than 5%, or less than 10 amino acids, and most desirably no amino acids being located at the outer ends beyond the polar and apolar parts.

In a preferred embodiment, the polar part of the amphiphilic polymer contains at least 10% (on the basis of the number of amino acids), preferably at least 15%, of polar amino acids selected from Arg, Asp, Lys, Glu, Asn, Gin and His, whereas the apolar part contains at least 10%, preferably at least 15%, of apolar amino acids selected from Phe, Met, Ile, Leu, Val Trp and Ala. In both parts, at least about 15, preferably at least 30% will be Gly, and at least 10% will be Pro. Preferably, the polar part contains less than 10% (more preferably less than 7%) of the apolar amino acids selected from Phe, Met, Ile, Leu, Val, Trp and Ala and the apolar part contains less than 10% (more preferably less than 7%) of the polar amino acids selected from Arg, Asp, Lys, Glu, Asn, Gln and His.

The amphiphilic polymer may also comprise alternating polar and apolar stretches, each stretch being e.g. between 5 and 100, preferably between 10 and 50 amino acids in length He number of alternating stretches may be two up to e.g. ten of such stretches (pairs of polar and apolar stretches). At least one polar stretch of such series, preferably two or more stretches, more preferably at least the terminal polar stretch, and most preferably each polar stretch has a polarity difference with the apolar stretch or preferably the apolar stretches as defined above. In this alternating arrangement, each pair of polar and apolar stretches may be separated from the next pair by an indifferent bridge of intermediate polarity.

Obviously an oil-in-water emulsion according to any of the embodiments of the invention described above as such or any combination thereof is covered by the invention Also any such oil-in-water emulsion can comprise further additives rendering it particularly suited to the application purpose of the emulsion. By way of example for the preferred application in photography, said additive can be selected from any of the following group of components, said group consisting of coupler, dye, organic solvent, inorganic solvent, surface/interface active agent, scavenger, UV absorber, optical brightener, stabiliser, pH controlling agent, mono/divalentions, In the case of application in foodstuffs, pharmaceuticals or cosmetics the additives must be non toxic i.e. pharmacologically acceptable to humans and/or animals.

Examples of protein-like structures, which can be applied for stabilisation of OW emulsions, are provided in the experimental description elsewhere, In the examples the improvement of the oil-in-water emulsion stability and the oil-in-water emulsion initial size is illustrated by use of various recombinant collagen-like polymers under various conditions. For example homodisperse molecules of varying sizes have been used. Molecules in which helical structure is absent have been used. Molecules with an pI of 9 have been used. The pH dependence and the T dependence of the OW emulsion stability and initial size are shown.

Oil-in-water emulsions are made by mixing a solution of collagen-like material in the hydrophilic phase with a hydrophobic phase. Mixing can be executed by siring, by high-pressure homogenisation, by treatment with ultrasonic frequencies, or the like. The hydrophobic phase can be any hydrophobic liquid suitable for the intended use. For example, trialkyl phosphates and triaryl phosphates such as trihexyl, trioctyl, tridecyl tris(butoxyethyl), tris(haloalkyl), trixylenyl and tricresyl phosphate, can be used for preparing photographic emulsions. Also phthalate esters, citric esters, benzoic esters, fatty acid esters and fatty acid amides, as well as hydrocarbons such as n-decane or n-dodecane can be used. Edible triglycerides derived from vegetable or animal fats can be used for preparing emulsions for use in nutritional, cosmetic and pharmaceutical products, etc. Surfactants, such as sodium dodecylbenzenesulphonate, can be added and oil-soluble components such as precursor molecules for dyes and UV absorbers, and further reducing reducing agents and other compounds can be added. Temperature can be varied. The protein-like material can consist of a pure component (homodisperse) or a mixture of components, all made by genetic engineering, or it can consist of a mixture of a component made genetic engineering and a traditional polymer. The invention covers a process comprising application of an oil-in-water emulsion according to any of the embodiments provided as oil-in-water emulsions according to the invention. Specifically the process can be a photography process or a foodstuff production process. Suitably a process according to the invention can be carried out at least at some stage in the presence of the oil-in-water emulsion at a pH below 6.0 preferably below 5.5 and suitably between 4.5–5.5. A process according to the invention can be carried out at some stage in the presence of the oil-in-water emulsion at a temperature below 40° C., suitably at ambient temperature i.e. between 10–30° C., suitably between 18–25° C. i.e. in absence of a heating step, preferably during the whole process. A process comprising a combination of any of the steps mentioned falls within process protection claimed. A process comprising any of the above mentioned measures, said process being storage of an oil-in-water emulsion according to any of the embodiments of the invention is also covered by the invention as is a process of preparation of any of the embodiments of the oil-in-water emulsion according to the invention.

General remarks about advantages of the application of the recombinant collagen-like polymers over traditional gelatins:

- Monodisperse products, creating the flexibility to design an OW emulsion with an optimal MW mix for creating steric hindrance without "bridge making" coagulation behaviour.
- Prevention of gelation behaviour (when indicated), creating freedom of processing temperature.
- Freedom to choose the isoelectric point and surface active behaviour (by polar/a-polar AA), which is for stabilisation and for robustness of stability in case of emulsion pH variations (=amphipolar collagen-like polymers).
- Freedom to use lower surfactant concentrations to obtain comparable or even improved stability.

The recombinant collagen like polypeptide as defined above can be produced by expression of a collagen-like polypeptide encoding nucleic acid sequence by a suitable microorganism. The process can suitably be carried out with a fungal cell or a yeast cell. Suitably the host cell is selected from the group consisting of high expression host cells like *Hansenula, Trichoderma Aspergillus, Penicillium, Neuro-* spora and *Pichia*. Fungal and yeast cells are preferred to bacteria as they are less susceptible to improper expression of repetitive sequences. Most preferably the host will not have a high level of proteases that attack the collagen structure expressed. In this respect *Pichia* offers an example of a very suitable expression system. Preferably the micro-organism is free of active post-translational processing mechanism for processing collagen like sequences to fibrils thereby ensuring absence of helix structure in the expression product, Also such a process can occur when the micro-organism is free of active post-translational processing mechanism for processing collagen like sequences to triple helices and/or when the nucleic acid sequence to be expressed is free of procollagen and telopeptide encoding sequences. The host to be used does not require the presence of a gene for expression of prolyl-4-hydroxylase the enzyme required for collagen triple helix assembly contrary to previous suggestions in the art concerning collagen production. The selection of a suitable host cell from known industrial enzyme producing fungal host cells specifically yeast cells on the basis of the required parameters described herein rendering the host cell suitable for expression of recombinant collagen according to the invention suitable for photographic applications in combination with knowledge regarding the host cells and the sequence to be expressed will be possible by a person skilled in the art.

Several strong and tightly-regulated inducible promoters are available for yeast systems and other recombinant production systems, allowing a highly efficient expression and minimising possible negative effects on the viability and growth of the host cells. When, for example, the methylotrophic yeast *Pichia pastoris* is used, the integrative can be incorporated into the yeast's genome after transformation of the host, resulting in genetical stability of the transformants (loss of plasmids is then of no importance). It is possible to generate transformants with the heterologous target gene under the control of e.g. the alcohol oxidase (AOX) promotor), in which the recombinant gene is either incorporated into the HTS4 locus or the AOX1 locus.

To ensure production of a non cleaved sequence a process according to the invention for producing recombinant collagen like material comprises use of a nucleic acid sequence encoding recombinant collagen amino acid sequence substantially free of protease cleavage sites of protease active in the expression host cell. In the case of *Pichia pastoris* for example and possibly also for other host cells a nucleic acid sequence encoding collagen of which the corresponding amino acid sequence is free of [Leu/Ile/Val/Met]-Xaa-Yaa-Arg wherein Xaa and Yaa correspond to Gly and Pro or other amino acids and at least one of the amino acids bet the brackets is amended could be preferred.

The process suitably provides expression leading to peptide harvest exceeding 2 g/liter or even exceeding 3 g/liter. The process can suitably be carried out with any of the recombinant collagen-like polypeptides defined above for the emulsion according to the invention. Multicopy transformants can provide more than 14 grams of gelatin per liter of clarified broth at a biomass wet weight of 435 grains per liter. Most suitably the product resulting from microbial expression is isolated and purified until it is substantially free of other protein, polysaccharides and nucleic acid. As is apparent from the examples numerous methods are available to the person skilled in the art to achieve this. The process according to the invention can provide the expression product isolated and purified to at least the following degree: content nucleic acid less than 100 ppm, content polysaccharides less than 5%, content other protein less than in commercial products. More preferably the DNA content of less than 1 ppm, RNA content less than 10 ppm even less than 5 ppm and polysaccharide content less than 0.5% or even less than 0.05% can be achieved.

The invention also concerns a process of producing an amphiphilic polymer in the manner described above, comprising introducing a gene encoding an amphiphilic polypeptide part of said polymer into a suitable host, culturing said host under conditions suitable for expression of said gene, and recovering said polypeptide. If desired the polypeptide can be coupled with another peptide or non-peptide, natural or synthetic polymer to produce a hybrid polymer suitable as an emulsifier.

In a preferred embodiment of the invention the gelatin-like material comprises no cysteine residues. The presence of cysteine in photographic product will disturb the product manufacturing process. It is thus preferred that cysteine is present in as small an amount as possible. Suitably photographic applications will employ material comprising less than 0.1% cysteine.

EXAMPLES

The production of gelatin 1 (MW=54 kD) and gelatin 2 (MW=28 kD), which can be used in the emulsions of the invention, is described in van Heerde et al. U.S. Pat. No. 6,150,081. These gelatins are referred therein as COLIA1-2 and COLIA1-1, respectively, and they are produced by transforming *Pichia pastoris* with mouse COLIA1-1 gene and expressing the gene by fermentation of the transformant *Pichia* strain.

Example 1

In this example the emulsification of current state-of-the-art gelatins A and B was compared with the invention (recombinant) gelatin 1 at pH=5.0 The average molecular weight of the de-ionised lime bone gelatin A and a hydrolysed gelatin B were respectively 177.4 and 23 kD, while the average molecular weight of the invention (recombinant) gelatin 1 was 54 kD.

The average molecular weight was measured via GPC analysis, the GPC method was carried out at 214 nm while the separation was performed over 300*7.8 mm column (TOSO Haas) loaded with TSK-gel 4000 SWXL, the eluent consisted of 1 wt % SDS, 0.1 mol/l $Na_2SO_4$ and 0.01 mol/$NaH_2PO_4$, at a flow of 0.5 m/min.

The basic recipe of each emulsion batch (in a total volume of 500 ml) contained 15 g gelatin 43 g tricresyl phosphate TCP oil and 435 gram of water. A surfactant amount of 0.4868 mM SDBS per 5 g gelatin per liter was added.

First the gelatin was dissolved in the necessary amount of water and pH was adjusted to the required pH of 5.0. After pH adjustment the required amounts of SDBS (from a 500 mmol/I SDBS stock solution) and TCP were added.

Emulsification was carried on 2 ml scale, therefore 2 ml sample was transferred to a plastic tube with a 10 ml capacity.

Pre-emulsification took place at 40° C. using a vortex mixer, final emulsification was carried out using a Branson Sonifier 250 ultra-soon emulsifier for 4 minutes.

For the ultra-soon emulsification a tip with 3 mm diameter was placed 0.5–1.0 cm below the upper emulsion level. Mixing with a too high severity and also higher (tan 0.5 cm below the upper emulsion level) tip position will cause foam and therefore inefficient energy transfer from tip to solution.

Initial size of the emulsions was measured immediately after emulsification, within 2 minutes, average size was measured via turbidity at λ=500 and λ=600 nm in a Hewlett Packard 8452A diode array spectrophotometer.

With a refractive index of TCP (=1.552) and the ratio of the turbidities at λ=600 nm and %λ=500 nm the average droplet size is calculated based upon the theory of Mie (described in the reference list).

Initial Size (in nm) at pH=5, Addition of 0.4868 mmol [SDBS] Surfactant/5 g Gelatin/Liter

| gelatin type | 15° C. | 25° C. | 40° C. |
|---|---|---|---|
| invention recombinant gelatin 1 (54 kD) | 318 | 303 | 198 |
| current state-of-the-art gelatin A (177 kD) | >500 | >500 | 450 |
| current state-of-the-art gelatin B (23 kD) | >500 | >500 | 280 |

This example shows that OW emulsions that are prepared with the invention (recombinant) gelatin 1 have a smaller initial size than OW emulsions prepared with traditional gelatins A and B at several temperatures. An advantage of the invention recombinant gelatin 1 is that they can be used for emulsion making at temperatures below 40° C., while very unstable emulsions are prepared at these temperatures with the state-of-the-art gelatins. No gelation occurs at temperatures below the 40° C. with the invention gelatin 1 because the proline is not hydroxylated while the pI of 9 for the invention gelatin is much more deviating than the state-of-the-art gelatins at pH=5. This temperature effect results in that the temperature control of the emulsification process is much easier and less critical The 'normal' setting temperature of current state of the art gelatin is about 30° C.

Example 2

In this example the emulsion ageing stability of current state-of-the-art gelatins A and B was compared at pH=6.0 with the invention (recombinant) gelatin 1 which has an average molecular weight of 54 kD.

The emulsion preparation and emulsification conditions were comparable to example 1. The only difference was that we measured size stability in time, this means that turbidity at λ=500 and at λ=600 nm was measured after 0 h, 1 h, 2 h, 3 h and 4 h after the emulsion was prepared. The size difference between 4 hours ageing and 0 hour ageing was plotted in the table below.

Ageing Properties of Recombinant Gelatin Compared to Traditional, State of the Art, Gelatin, pH 6.0, 0.4868 mMol [SDBS]/5 g Gelatin/l. The Size Difference is Defined as the Difference in Size (in nm) Between 4 and 0 Hours (Fresh) of Ageing.

| | 15° C. | 25° C. | 40° C. | |
|---|---|---|---|---|
| invention recombinant gelatin 1 (54 kD) | 100 | 159 | 158 | nm |
| current state-of-the-art gelatin A | >500 | >500 | 247 | nm |
| current state-of-the-art gelatin B | >500 | 190 | 200 | nm |

This example shows that the size stability of the OW emulsion stabilised with recombinant gelatin 1 is better than the stability of an OW emulsion stabilised with traditional current state-of-the-art gelatins A and B.

From the example it is clear that a temperature decrease of the OW emulsion to 15° C. increases the size stability significantly with the invention (recombinant) gelatin 1. This temperature decrease can not be realised with the traditional gelatins because gelation happens. So the absence of gelation makes a temperature shift in the production process possible (e.g. transfer of the emulsion to a "Waiting tank" to increase the size stability before use in the "final emulsion").

The same results were visible at pH 5.0; the invented recombinant gelatin gives due to its higher pI more flexibility in the pH of the emulsification process,

Example 3

In this example traditional gelatin A and recombinant gelatin 1 are mixed in various ratios, to show the possibility that not only recombinant gelatin but also mixtures of recombinant and traditional gelatins can be used.

The mixtures were prepared by mixing the proper ratios of solutions of traditional and recombinant gelatin before emulsification.

Emulsion preparation, emulsification conditions and size measurements were carried out in the same way as described in examples 1 and 2.

Test Conditions: pH=6.0, 40° C. Addition of 0.4868 mmol [SDBS]/5 g Gelatin/Liter. The Size Ageing is Defined as the Difference in Size (in nm) Between 4 and 0 Hours (Fresh) Ageing.

| | Ageing 0->4 h | |
|---|---|---|
| invented recombinant gelatin 1 (54 kD) | 158 | nm |
| mix recombinant 54 kD/current gelatin A in ratio 1/1 | 222 | nm |
| mix recombinant 54 kD/current gelatin A in ratio 1/3 | 218 | nm |
| current state-of-the-art gelatin A | 247 | nm |

This example shows that the improved size stability of the OW emulsion can also be obtained with mixtures of the invented (recombinant) gelatins and the traditional gelatin A.

The stability increase of the mixtures is less pronounced compared to the stability of only recombinant gelatin however improved stability is still visible.

Example 4

In this example the emulsion size stability after ageing for 4 hours of current state-of-the-art gelatin A was compared with the invention recombinant gelatin 1 at various surfactant [SDBS]-concentrations and at pH=6.0.

The emulsions are prepared in the same way as described in the examples 1, 2 and 3, the only difference is that the [SDBS] is adjusted to the required [SDBS] by adding more amount of SDBS from a 500 mmol/l [SDBS] stock solution.

Emulsification and size measurements in be are also measured in the same way as described in the previous mentioned examples.

Ageing at Various [SDBS] at pH 6.0 and 40° C. The Difference is Defined as the Difference Between the Size after 4 and after 0 Hours Ageing.

| [SDBS] mmol/5 g gelatin/litre | recombinant gelatin 1 (54 kD) | current state-of-the-art gelatin A | |
|---|---|---|---|
| 0.064 | 245 | 280 | nm |
| 0.4868 | 158 | 247 | nm |
| 0.854 | 240 | 263 | nm |
| 3.5 | 360 | 370 | nm |
| 20 | 430 | 410 | nm |

The improved stability of the invented (recombinant) gelatin is clearly visible at [SDBS] below 1 mmol/⅕ g gelatin, above this concentration the gelatin concentration at the interface is decreasing and is therefore less important in stability.

These results indicate that the same or even improved stability for recombinant gelatin compared to traditional gelatin can be obtained at lower [SDBS], see figure.

Example 5

In this example the initial size of emulsions prepared with current state-of-art gelatin A was compared at pH 5.0 with two invention (recombinant) gelatins 1 and 2 with average molecular weights of respectively 54 and 28 kD. The preparation of the emulsions, but also the size measurements was done in the same way as described in example 1.

Initial Size of Emulsions Prepared with Different Recombinant Molecular Weight Gelatin. Emulsion pH=5.0; [SDBS]=0.4868 mM/5 g Gelatin/Liter

| samples | initial size (in nm) |
|---|---|
| Invention recombinant gelatin 3 (57 kD with amphiphilic character | 150 |
| Invention recombinant gelatin 1 (54 kD) | 198 |
| Invention recombinant gelatin 2 (28 kD) | 290 |
| Current state of the art gelatin A | 450 |

This experiment shows that the initial size of the OW emulsion is significantly improved when recombinant gelatins are applied already with a molecular weight of 28 kDa. Invented gelatins with a higher molecular weight of 54 kDa enables further improvement for the initial size of the OW emulsion The lowest initial size has been realised with the invented (recombinant) gelatin with a MW of 57 kDa, which has an amphipolar bi-functional character. This bi-functional character is obtained by a collagen, which is synthetically made from two a-polar building blocks (called N1 and N2) and one polar block (called P1). The blocks are combined as N1N2P1P1P1P1 such that the total polar P-"leg" sticks into the water-phase and the apolar N1N2-"leg" is adsorbed at the oil-interphase. The lowest initial size of the OW-emulsion has been achieved with this new developed bi-functional collagen. The synthesis route of this invented gelatin with an amphipolar character is described in the following text.

Example 6

Materials and Methods and Analysis of Amphiphilic Recombinant Collagen-like Polymer.

General Molecular-biological Techniques

Cloning procedures were performed essentially according to Maniatis et al. [1]. Plasmid DNA was isolated using Wizard Plus SV miniprep, or Qiagen midiprep systems. DNA was isolated from agarose gels using the QIAquick Gel Extraction Kit (Qiagen). All enzymes used were from Amersham Pharmacia Biotech unless otherwise stated and were used according to the manufacturer's recommendations. All procedures involving the handling and transformation of *Pichia pastoris* were essentially performed according to the manual of the *Pichia* Expression Kit (Invitrogen) [2].

Construction of pPIC9-N1N1$P_4$ and pPIC9-N1N2$P_4$

Custom-designed amphiphilic gelatins were constructed by combining polar and nonpolar modules. Each module has a molecular weight of approximately 10 kDa. The design is such that in principle, any combination and number of modules can be combined in any order desired. Molecules consisting of two nonpolar modules and four polar modules (P) were constructed. One molecule (N1N1$P_4$) contains two identical nonpolar modules (N1). Another molecule (N1N2$P_4$) contains two different nonpolar modules (N1 and N2). The N2 module is similar to the N1 module, but differs mainly in the presence of a cluster of methionine and charged residues at its C-terminal side.

The polar gelatin module (P monomer) was constructed as described in van Heerde et al. U.S. Pat. No. 6,150,081 where it is used in base emulsion applications [3]. The gene was designed to have the codon usage of *Pichia pastoris* highly expressed genes (Sreekrishna and Kropp [4]). Two separate PCR reactions were performed, using the following oligonucleotides:

1. 1 pmol OVL-PA-FW, 1 pmol OVL-PA-RV, 50 pmols HLP-PA-FW and 50 pmols HLP-PA-RV.
2. 1 pmol OVL-PB-FW, 1 pmol OVL-PB-RV, 50 pmols HLP-PB-FW and 50 pmols HLP-PB-RV.

The 50 μl PCR reactions were performed in a GeneAmp 9700 (Perkin-Elmer) and contained 0.2 mM dNTP's (Pharmacia), 1× Pwo buffer (Eurogentec) and 1.25 U Pwo polymerase (Eurogentec). Reaction 1 involved 18 cycles consisting of 15 seconds at 94° C. and 15 seconds at 72° C. Reaction 2 involved a touchdown PCR, whereby each cycle consisted of 15 seconds at 94° C., 15 seconds at the annealing temperature and 15 seconds at 72° C. The annealing temperature was lowered from 72° C. to 68° C. in the first 5 cycles, after which 20 additional cycles at an annealing temperature of 67° C. were performed.

The PCR products were isolated from agarose gel, 0.3 pmols of each fragment and 50 pmols of the outer primers HLP-PA-FW and HLP-PB-RV were subjected to overlap extension PCR 25 cycles consisting of 15 seconds at 94° C., 15 seconds at 67° C. and 15 seconds at 72° C. were performed. The resulting 0.3 kb PCR fragment was digested with XhoI/EcoRI and inserted in cloning vector pMTL23. An errorless clone was selected by verification of the sequence by automated DNA sequencing.

In order to create a P tetramer for the polar part of the amphiphilic gelatins, the P module was released by digesting the vector with DraIII/Van91I. In a separate reaction the vector was digested with Van91I and dephosphorylated. The DraIII Van91I fragment was then inserted into his Van91I digested vector. This yielded a vector containing a P dimer. This dimer was released by digestion with DraIII/Van91I and reinserted into the Van91I site of the dimer bearing vector, yielding pMTL23-$P_4$.

Analogous to the construction of the polar P momoner gelatin, two different nonpolar gelatins N1 and N2, respectively, were constructed. The genes were designed to have the codon usage of *P. pastoris* highly expressed genes (Sreekrishna and Kropp [4]). Two separate reactions were performed for both N1 and N2, using the following oligonucleotides:

N1:

1. 1 pmol OVL-NA-FW, 1 pmol OVL-N1A-RV, 50 pmols HLP-PA-FW and 50 pmols HLP-N1A-RV.
2. 1 pmol OVL-N1B-FW, 0.1 pmol OVL-N1B-RV, 50 pmols HLP-NIB-FW and 50 pmols HLP-PB-RV.

N2:

3. 1 pmol OVL-NA-FW, 1 pmol OVL-N2A-RV, 50 pmols HLP-PA-FW and 50 pmols HLP-N2A-RV.
4. 1 pmol OVL-N2B-FW, 1 pmol OVL-N2B-RV, 50 pmols HLP-N2B-FW and 50 pmols HLP-PB-RV.

Reaction conditions for N1 and N2 module reactions 1, 3 and 4 were as for P monomer reaction 2. The first 5 cycles of N1 module reaction 2 consisted of 15 seconds at 98° C. and 15 seconds at 72° C. without presence of primers HLP-NIB-FW and HLP-PB-RV. These primers were then added and 20 cycles consisting of 15 seconds at 94° C. and 15 seconds at 72° C. were performed.

The PCR products were purified from agarose gel and overlap extension PCR was performed using 0.3 pmols of each fragment and 50 pmols of the outer primers HLP-PA-FW and HLP-PB-RV. Each PCR cycle consisted of 15 seconds at 94° C., 15 seconds at the annealing temperature and 15 seconds at 72° C. The annealing temperature was lowered from 72° C. to 68° C. in the first 5 cycles, after which 20 additional cycles at an annealing temperature of 67° C. were performed. The resulting 0.3 kb PCR fragments were digested with XhoI/EcoRI and inserted in cloning vector pMTL23, yielding vectors pMTL23-N1 and pMTL23-N2. Errorless clones were selected by verification of the sequence by automated DNA sequencing.

Vector pMTL23-N1 was digested with DraIII and dephosphorylated, after which one DraIII/Van91I digested N1 module was inserted to form pMTL23-N1N1. Likewise, one DraIII/Van91I digested module was inserted in DraIII digested and dephophorylated vector pMTL23-N2 to form vector pMTL23-N1N2. The N1N1 and N1N2 modules were released by digestion with DraIII/Van91I and were ligated into DraIII digested and dephosphorylated pMTL23P4 to yield constructs pMTL23-N1N1$P_4$ and pMTL23-N1N2$P_4$, respectively. The resulting N1N1$P_4$ and N1N2$P_4$ inserts were then released by digestion with XhoI/EcoRI and cloned in the XhoI/EcoRI sites of *Pichia* expression vector pPIC9. The encoded amino acid sequence of the mature (processed) N1N1$P_4$ and N1N2$P_4$ gelatins are provided in the sequence listing that follows:

N1N2$P_4$ has a theoretical molecular weight: 57 kD, isoelectric point: 5.8

N1N1$P_4$ has a theoretical molecular weight: ca 57 kD, isoelectric point: 4.9

Transformation of *Pichia pastoris* with pPIC9—N1N1$P_4$ and pPIC9-N1N2$P_4$

In order to obtain $Mut^+$ transformants upon transformation of *P. pastoris* (i.e. fast-growing on methanol), the constructs were linearized with SalI in order to target integration of the construct into the his4 gene, keeping the AOX1 locus intact [2]. It will be understood that $Mut^S$ transformants (i.e. slow-growing on methanol) can in principal also be used, but $Mut^+$ was chosen for practical reasons.

After phenol extraction and ethanol precipitation, the construct was then used to transform *P. pastoris* strain GS115 (Invitrogen) using electroporation according to Becker and Guarente [5] using the BioRad GenePulser (set at 1500V, 25 μF and 200 Ω and using 0.2 cm cuvettes). The transformation mix was plated out on Minimal Dextrose plates (MD-plates; 1.34% YNB, $4\times10^{-5}$% biotin, 1% dextrose and 1.5% agar) in order to select for the presence of the vector which converts the $His^-$ strain GS115 to $His^+$. After growth at 30° C. for 3 days, several colonies were selected for PCR confirmation of the $Mut^+$ genotype. The PCR machine used was the Perkin-Elmer GeneAmp 9700. Colony PCR was performed using 50 pmol 5'AOX1 primers Seq id nr. 24, 50 pmol 3'AOX1 primer Seq id nr 25, 1.25 U Taq polymerase (Pharmacia), 0.2 mM dNTPs (Pharmacia) and 1× Taq buffer (Pharmacia) in a total volume of 50 μl. After an initial denaturation at 94° C. for 5 minutes, 30 cycles were performed consisting of 15 seconds at 94° C., 30 seconds at 57° C. and 2 minutes at 72° C. Final extension was at 72° C. for 10 minutes. Agarose gel electrophoresis should reveal a 2.2 kb endogenous AOX1 band for $Mut^+$ transformants.

Production of N1N1$P_4$ and N1N2$P_4$

Selected transformants were fermented in fed-batch mode according to the *Pichia* fermentation guidelines of Invitrogen. Cells were grown in a 1-liter fermentor (Applikon) in the initial experimental stages to optimise protein production. Thereafter cells were grown in a 20-liter or a 140-liter fermentor (Biobench 20, Bio-pilot 140, Applikon) for pilot scale production of gelatin. Working volumes were 1-liter, 15-liter and 100-liter, respectively. AD1020 controllers (Applikon) were used to monitor and control the fermentation parameters. The program BioXpert (Applikon) was used for data storage. Dissolved oxygen levels were monitored in the fermentor using an oxygen electrode (Ingold for 1-liter fermentations, Mettler Toledo for larger scale fermentations). Agitation (500–1000 rpm) and aeration (1–2 vvm, i.e. 1–2 $LL^{-1}min^{-1}$) were manually adjusted to keep the dissolved oxygen concentration above 20%. pH was measured by a pH electrode (Broadly James cooperation) and automatically kept at pH 3.0 by addition of ammonium hydroxide (25%), which also served as nitrogen source for growth of the micro organisms. An anti-foam-electrode was used to prevent excessive foaming When necessary, the anti foam Structol J673 (Schill and Seilacher, Hamburg, Germany) or the organic anti foam 204 (from Sigma_Aldrich, Bornem, Belgium) was used. Growth of the micro-organisms was monitored by determination of the cell dry weight. A calibration curve was made by means of which cell wet weight could be converted into cell dry weight. Cell wet weight was determined after centrifugation of 2 ml samples for 5 min at 15,000 rpm and removing the supernatant. Cell dry weight was determined after addition of 200 μl of cells to a pre-dried filter (0.45 μm membrane, Schleicher & Schüll, Dassel, Germany), washing with 25 ml of deionized water and drying in a microwave oven for 15 minutes at 1000 W. Cell dry weight was approximately a factor 3 lower than cell wet weight. Precultures were started from colonies on a MGY plate, in flasks containing a total of 10% of the initial fermentation volume of MGY. The volume of the medium was ≦20% of the total flask volume. Cells were grown at 30° C. at 200 rpm in a rotary shaker for 24–60 hours.

The fermentation basal salts medium in the fermentor contained per liter; 26.7 ml of phosphoric acid (85%), 0.93 g calcium sulphate, 18.2 g potassium sulphate, 14.9 g magnesium sulphate.$7H_2O$, 4.13 g potassium hydroxide and 40.0 g glycerol. An amount of 4.3 ml of $PTM_1$ trace salts was added per liter of fermentation basal salts medium. $PTM_1$ trace salts contained per liter: 4.5 g cupric chloride.$2H_2O$, 0.09 g potassium iodide, 3.5 g manganese chloride.$4H_2O$, 0.2 g sodium molybdate.$2H_2O$, 0.02 g boric acid, 1.08 g cobalt sulphate.$7H_2O$, 42.3 g zinc sulphate.$7H_2O$, 65.0 g ferrous sulphate.7HO, 0.2 g biotin and 5.0 ml sulphuric acid. Trace salts were filter sterilised.

The fermentor was sterilised with the fermentation basal salts medium. The 20-liter and 120-liter fermentor were sterilised in situ with initial medium volumes of 5–7.5 l and 50-liter, respectively. The 1-liter fermentor was sterilised with 500 ml medium in an autoclave. After sterilisation the medium was supplemented with sterile 1% casamino acids (optional).

The temperature was set at 30° C., agitation and aeration were set at 500 rpm and 1 vvm (i.e. 1 $LL^{-1}min^{-1}$), respectively. The pH was adjusted to set point (pH 5.0) with 25% ammonium hydroxide. Trace salts were aseptically added to the medium. The fermentor was inoculated with 10% of the initial fermentation volume of precultured cells in MGY. The batch culture was grown until the glycerol was completely consumed (18–24 hours). This was indicated by an increase of the dissolved oxygen concentration to 100%. Cell dry weight was 25–35 g/l in this stage. Thereafter the glycerol fed-batch phase was started by initiating a 50% (v/v) glycerol feed containing 12 ml $PTM_1$ trace salts per liter of glycerol. The glycerol feed was set at 18 ml/h/liter initial fermentation volume. The glycerol feed was carried out for 4 hours, or overnight in the case of a long lag phase. During the glycerol batch phase the pH of the fermentation medium was lowered to 3.0.

An additional 1% of casamino acids were added (optional) after which the protein induction phase was initiated by staring a 100% methanol feed containing 12 ml $PTM_1$ trace salts per liter of methanol. The feed rate was set to 3 ml/h/liter initial fermentor volume. During the first hours methanol accumulated in the fermentor. After 2–4 hours dissolved oxygen levels decreased due to adaptation to methanol. The methanol feed was increased to 6 ml/h/initial fermentor volume in the case of a fast dissolved oxygen spike. If the carbon source is limiting, shutting off the carbon source causes the culture to decrease its metabolic rate and the dissolved oxygen concentration to rise (spike). After an additional 2 hours the methanol rate was increased to 9 ml/h/liter initial fermentor volume. This feed rate was maintained throughout the remainder of the fermentation. The fermentation was stopped after 70–130 h methanol fed-batch phase. During the fermentation samples were taken of 2 ml, centrifuged (5 min, 15,000 rpm) and the supernatant was stored at −20° C.

At the end of the fermentation, the cells were removed by centrifugation (10,000 rpm, 30 min, 4° C.), followed by micro filtration (cut off 0.2 μm) in the case of the 1-liter fermentation. Cells were removed by micro filtration in the case of the 20- or 100-liter fermentation.

In the case of 20-L fermentation, the cell broth was applied to a microfiltration module containing a poly ether sulphone membrane with 0.20 μm pore size (type MF 02 M1 from X-Flow, fitted in a RX 300 filtration module from X-Flow). In the case of the 100-liter fermentation cells were removed by a pilot plant scale cross flow micro filtration unit containing a hollow fiber poly ether sulphone membrane with 0.2 p pore size (type MF 02 M1, from X-Flow, fitted into a R-10 membrane module). These filtration units are mentioned merely as examples. It will be understood that any suitable micro filtration system could be applied to remove the cells. Optionally, the bulk of cells and debris was removed by centrifugation, and only the supernatant and the medium used to wash the cells was applied to the micro filtration units.

In the case of the 100 Liter fermentation, the cell broth was first applied to a filtration unit fitted with a stack of flat 0.4×0.4 m cellulose Bio 10 or Bio 40 depth filters (USF Seitz Filter Werke, Bad Kreutznach, Germany) with a total filtration surface of 1.9 $m^2$. Thereafter, the permeate was filtered with a spiral wound 0.2 μm pore size poly sulphone dead end micro filtration unit (USF Seitz Filter Werke, Bad Kreutznach, Germany). After micro filtration, the filters were sterilised, the cells were destroyed by steam sterilisation or by autoclaving, and the absence of recombinant *Pichia* cells in the filtrate was verified by plating out samples of filtrate.

Purification of Synthetic Gelatins from the Cell Free Fermentation Broth Separation of Recombinant Amphiphilic Gelatins and Non-Recombinant *Pichia* Proteins or Small Peptides (Optional).

For separation of recombinant amphiphilic gelatins and non-recombinant *Pichia* proteins, cell-free fermentation broth was subjected to differential precipitation (=fractionation) at 40–80 volume- % ethanol or acetone. At 40 volume- % ethanol or acetone, the non-gelatinous proteins (from *Pichia*) were precipitated, while at 60–80 volume- % ethanol or acetone, gelatin was precipitated, as shown by SDS-PAGE and analysis of the amino acid composition. Small peptides and other low molecular weight contaminants remained in solution at 80 vol.- % ethanol or acetone. Ethanol or acetone was cooled for 2–4 hours at −20° C. An amount of 40 vol.- % of ice-cold ethanol or acetone (v/v) was added slowly to the pre-cooled supernatant from the fermentation at 4° C. under magnetic stirring. Supernatant was stirred overnight at 4° C. Precipitated proteins and particles were removed by centrifugation (4° C., 10.000 rpm, 30 min). The pellet was resuspended in 40 vol.- % ice-cold ethanol or acetone and again centrifuged. Both 40 vol.- % acetone supernatant fractions were pooled. Thereafter the supernatant was brought to 60–80 vol.- % ethanol, or acetone (v/v) and stirred overnight. Precipitated proteins were collected by centrifugation. The pellet was dissolved in an appropriate amount of water. In addition to ultra filtration or evaporation of water, precipitation of gelatin at 80% (70–90%) ethanol or acetone can also be used to concentrate the protein.

Purification of Recombinant Gelatin from Fermentation Broth by Anion Exchange Chromatography.

At laboratory (mg to g) scale, the recombinant gelatin was optionally captured and purified from the fermentation broth by anion exchange chromatography (e.g. using Q Sepharose BP or XL from Amersham Pharmacia Biotech, Uppsala, Sweden), preferably in 20 mM phosphate, carbonate or borate buffer at pH 6 to 8 and using a NaCl gradient or step gradient for elution.

Purification of Recombinant Gelatin from Cell Free Fermentation Broth by Ammonium Sulphate Precipitation.

The recombinant gelatin was purified from non-recombinant proteins and peptides, polysaccharides, nucleic acids and other contaminating molecules by selective precipitation of the gelatin at 60% saturation of ammonium sulphate. Ammonium sulphate was slowly added to 60% saturation at 4° C. After 60 min stirring the sample was centrifuged (30 min, 4° C., 10,000 rpm). The pellet was resuspended in 60% ammonium sulphate and again centrifuged. If more than 1% (w/w) polysaccharides or sugars remained present, the ammonium sulphate precipitation procedure described above was repeated after complete redissolving of the gelatin in the absence of ammonium sulphate.

Alternatively, the ammonium sulphate precipitate was collected on a suitable depth filter (e.g. Bio 10, Bio 40, or AKS5 from USF Seitz Filter Werke, Bad Kreuznach, Germany) and washed flee from contaminating components by flushing the filter and filter cake with 60–70% ammonium sulphate.

Finally, the purified gelatin pellet or filter cake was dissolved in deionised water.

At laboratory scale, milligram to gram quantities of purified recombinant gelatin were desalted by dialysis against deionised water, which was refreshed every 4 hours. Dialysis membranes of regenerated cellulose (Spectra Por®, from Spektrum) were used with a molecular weight cut-off of 8 kD. The dialysis was stopped after 2–7 days when the electrical conductivity of the sample was judged to be sufficiently low.

At pilot scale (i.e. gelatin quantities of more than 10 to 100 gram), the purified recombinant gelatin was desalted by ultrafiltration/diafiltration, using poly ether sulphone membranes with a molecular cut-off of 4 (1 to 10) kD. The ultrafiltration-diafiltration was stopped when the electrical conductivity of the gelatin solution was sufficiently low. This typically occurred after 10 to 30 cycles of dilution (2×) and concentration (2×).

Optionally, an additional, final desalting step was carried out by adding a slight excess of mixed-bed ion exchange resin beads (e.g. Amberlite MB-3 from Merck, Darmstadt, Germany) and incubating for 30 mL to maximally 1 hour.

Conductivity was measured with a digital conductivity meter (Radiometer), calibrated with 1 mM and 10 mM KCl solutions (140 and 1400 $\mu S.cm^{-1}$, respectively). After desalting by dialysis or diafiltration, the final electrical conductivity was typically 5 to 15 $\mu S.cm^{-1}.((\text{gram gelatin}).L^{-1})^{-1}$. After further desalting with mixed bed ion exchange beads, the final electrical conductivity was typically 0.5 to 3 $\mu S.cm^{-1}.((\text{gram gelatin}).L^{-1})^{-1}$.

Where applicable, the product was pre-dried (optional) by precipitation with high concentrations of acetone and evaporation of the acetone.

The purified and desalted product was either freeze-dried or spray-dried.

Characterisation of the Gelatin Product

Molecular Weight Distribution and Contaminating Proteins

The molecular weight distribution of the recombinant gelatin product and the presence of contaminating proteins were analyzed by denaturing poly acrylamide gel electrophoresis (SDS-PAGE) [6] in a Mini-PROTEAN II system (from Biorad) and Coomassie Brilliant blue staining. Optionally, a higher voltage was applied (400 Volt), in order to speed-up the electrophoresis rate and minimize protein diffusion. For both amphiphilic gelatin types a single gelatin band was observed. After purification as described above (e.g. micro filtration, ammonium sulphate fractionation and desalting), the product was apparently homogeneous and free from contaminating proteins.

The molecular weight apparent from SDS-PAGE, as calibrated with globular protein molecular weight markers, was too high, in accordance with numerous other observations on gelatins and collagen-like proteins and polypeptides.

However, after gel filtration of the ammonium sulphate-purified gelatin with a Superose-12 column (Amersham Pharmacia Biotech, Uppsala, Sweden), a single gelatin peak eluted at the correct theoretical molecular weight, with reference to a set of 6 distinct fragments of recombinant mouse type I collagen, having known (i.e. theoretical and experimentally verified) molecular weights of 8, 12, 16, 28, 42 and 54 kDa. The gelatin samples were eluted from the Superose-12 column with 100 mM NaCl and a flow of 0.2 mL/min. This showed that the recombinant gelatin product was correctly expressed and was not degraded to any considerable extent The correctness of molecular weight was confirmed by mass spectrometry.

Confirmation of N-terminal Amino Acid Sequence

After SDS-PAGE as described above, the proteins in the gel were blotted onto an Immobilon $P^{SQ}$ membrane (from Millipore) by applying 100 V for one hour in a Mini Trans-Blot Cell (Biorad). Transfer buffer was 2.2 g CAPS per liter of 10% methanol, pH 11. Blots were stained with Coomassie Brilliant Blue and selected bands were cut out. N-terminal protein sequencing was performed by Edman degradation. It appeared that the N-terminal sequence of both recombinant gelatin products was correct.

Confirmation of Purity and Amino Acid Composition

The amino acid composition of the purified gelatin product was determined after complete HCl-mediated hydrolysis of the peptide bonds at elevated temperature, followed by derivatisation of the amino acids with a fluorophore, and HPLC.

The percentage Gly expected from pure gelatin is 33%. This offers a means of estimating the purity of produced recombinant gelatins. In order to correct for the percentage of Gly in endogenously secreted proteins of *P. pastoris*, amino acid composition analysis was performed on fermentation supernatant of a $Mut^{+}$ transformant of pPIC9. The percentage Gly found was 9%. The purity of a sample can now be estimated by the formula:

$$(\%\ \text{Gly}-9)/(33-9)=(\%\ \text{Gly}-9)/24.$$

Determination of Contamination with Polysaccharides, Sugars and Nucleic Acids After dissolution of samples in MiliQ water, the following assays were performed. The sugar content was determined by a phenol-based assay. 200 μL samples were mixed with 200 μl 5% (w/w) phenol. After thorough mixing using a Vortex mixer, 1 mL of concentrated sulphuric acid was added After mixing, the samples were incubated for 10 min at room temperature and, subsequently, for 20 min. at 30° C. After cooling, the light absorption of the samples at 485 nm was determined. Analytical grade mannose was used to prepare the calibration curve.

The DNA content was determined by mixing aliquots of diluted SYBR® Green I nucleic acid 'gel' stain (10,000× conc. In DMSO) from Molecular Probes with our samples. After thorough spectral analysis, the excitation wavelength was chosen to be 490 nm, and the emission wavelength 523 nm. The calibration was by subsequent addition of known amounts of DNA to his same mixture, as internal standards. Thus, a calibration curve was constructed. Furthermore, it was checked that subsequent addition of DNA-degrading enzyme resulted in complete break down of the fluorescent signal.

A quantitative indication of the RNA plus DNA-content was subsequently obtained by using SYBR® Green II 'RNA gel stain', instead of SYBR® Green I. After thorough spectral analysis, the excitation wavelength was chosen to be 490 nm, and the emission wavelength 514 nm. Calibration was by subsequent addition of known amounts of RNA. The resulting value was pronounced to be the 'RNA' content of the sample. In the absence of DNA, it corresponded to the true RNA content. When present, the DNA-associated fluorescence may have biased the RNA values, although a final addition of RNAse was used to discern the DNA- and RNA-derived contributions to the fluorescence.

Quantification of the Recombinant Product

The protein content was determined by the BCA assay from Pierce, using gelatin from Merck (Darmstadt, Germany) as a reference. The gelatin content of the cell-free fermentation broth and various semi-purified gelatin samples was determined by fractionating the samples at 40 and 80 volume- % of ethanol or acetone, as described above, and quantifying the protein content of the 40% pellet (i.e. non-recombinant *Pichia* protein), the pellet obtained by enhancing the solvent content of the 40% supernatant to 80 vol.- % (i.e. precipitated recombinant gelatin), as well as the 80% supernatant (small peptides and bias from other molecules). Again the BCA assay from Pierce was applied, using gelatin from Merck as a reference. The purified and dried product was in addition quantified by weight determination.

Results:

Gelatin Batch Produced at Laboratory Scale (Example)

about 1 gram purification: micro filtration, $(NH_4)_2SO_4$, desalting by dialysis, lyophilisation.

DNA: 2 ppm (w/w)

RNA: 10 ppm (w/w)

total sugars: 1% (w/w)

purity calculated from amino acid composition determination conductivity: 5 $\mu S.cm^{-1}.((\text{gram gelatin}).L^{-1})^{-1}$ gelatin was single-component according to SDS-PAGE and FPLC.

References Cited

[1] Maniatis T., Fritsch, E. F. & Sambrook, J. (1982) Molecular cloning: A laboratory manual. Cold Spring Harbor Laboratory, Cold Spring Harbor, N.Y.

[2] Manual of the *Pichia* Expression Kit Version E (Invitrogen, San Diego, Calif., USA).

[3] EP-A-0926432, NL-A-1007908 and EP-A-1014176, all non-prepublished.

[4] Sreekrishna, K. and Kropp, K. E. (1996) *Pichia pastoris*, Wolf, K. (Ed), Nonconventional yeasts in biotechnology. A handbook, Springer-Verlag, pp. 6/203-6/253.

[5] Becker, D. M. & Guarente, L. (1991) High efficiency transformation of yeast by electroporation. Methods in Enzymology, vol. 194: 182–187.

[6] Laemmli, U. K (1970) Cleavage of structural proteins during the assembly of the head of bacteriophage T4. Nature 227: 680–685.

What is claimed is:

1. A process for preparing an oil-in-water-emulsion having a composition including, in an amount sufficient to stabilize the emulsion, a collagen-like recombinant peptide, the collagen-like recombinant peptide comprising at least one GXY domain having a length of at least 5 consecutive GXY triplets, wherein X and Y each represents an amino acid, and wherein at least 20% of the amino acids of said recombinant collagen-like peptide are present in the form of consecutive GXY triplets.

2. A process for preparing an oil-in-water emulsion according to claim 1 further comprising combining the oil-in-water emulsion with one or more pharmaceutically suitable ingredients to provide a pharmaceutical product.

3. Process according to claim 1, wherein said recombinant collagen-like peptide is free of helix-structure.

4. Process according to claim 1, wherein said recombinant collagen-like peptide has an isoelectric point at least 0.5 pH units removed from the pH of said oil-in-water emulsion.

5. Process according to claim 1, wherein said recombinant collagen-like peptide has an isoelectric point of 4 or 10 or anywhere between 4 and 10.

6. Process according to claim 1, wherein said recombinant collagen-like peptide has a molecular weight of at least 2.5 kDa up to 100 kDa.

7. Process according to claim 1, wherein said recombinant collagen-like peptide is homodisperse with regard to the molecular weight of the peptide.

8. Process according to claim 1, wherein said recombinant collagen-like peptide further comprises non-recombinant collagen.

9. Process according to claim 1, wherein said recombinant collagen-like peptide exhibits an amphiphilic structure, with at least one part of the molecule being polar due to the presence of a sufficient number of polar amino acid residues to render that part polar and the other part being apolar due to the presence of a sufficient number of apolar amino acid residues to render that part apolar and wherein said polar part contains at least 10 polar amino acids and said apolar part contains at least 10 apolar amino acids.

10. Process according to claim 9, wherein the lengths of at least one polar part and of at least one apolar part are each at least 10% of the peptide backbone.

11. Process according to claim 9, wherein the average transfer free energy per amino acid of at least one polar part is at least 0.3 kcal/mole lower than the average transfer free energy per amino acid of at least one apolar part.

12. Process according to claim 1, wherein said oil-in-water emulsion exhibits a smaller initial droplet size than 500 nm at a temperature of 40° C. or less and at pH=5.

13. Process according to claim 12, wherein said oil-in-water emulsion exhibits a smaller increase in droplet size after 4 hours than 400 nm at a temperature of 40° C. or less and at a pH=5.

14. Process according to claim 1, wherein said recombinant collagen-like peptide is present in a concentration in the range from about 2 to about 100 g/l solvent.

15. Process according to claim 1, wherein said recombinant collagen-like peptide exhibits viscosity in the range of 0.005–8 mP when dissolved at a concentration of 6.6% in water at a temperature of 40° C.

16. Process according to claim 1, wherein said recombinant collagen-like peptide does not exhibit gelation at a temperature below 30° C.

17. A pharmaceutical product prepared by the method according to claim 2.

18. In combination, an oil-in-water emulsion and a product ingredient, wherein the oil-in-water emulsion comprises a recombinant collagen-like peptide in an amount sufficient to act as a stabilizer of said emulsion and wherein said recombinant collagen-like peptide comprises at least one GXY domain having a length of at least 5 consecutive GXY triplets, wherein X and Y each represent an amino acid, and wherein at least 20% of the amino acids of said recombinant collagen-like peptide are present in the form of consecutive GXY triplets, and wherein the product ingredient comprises a nutritionally or pharmaceutically or cosmetically suitable ingredient.

19. The combination according to claim 18, wherein said recombinant collagen-like peptide exhibits an amphiphilic structure, with at least one part of the molecule being polar due to the presence of a sufficient number of polar amino acid residues to render that part polar and the other part being apolar due to the presence of a sufficient number of apolar amino acid residues to render that part apolar.

20. The combination according to claim 18, wherein said recombinant collagen-like peptide is present at a concentration in the range from about 2 to about 100 g/l solvent.

21. The combination according to claim 18, wherein said recombinant collagen-like peptide is free of hydroxyproline.

22. The combination according to claim 18, wherein at least 5% of X and / or Y are proline.

23. The combination according to claim 18, wherein between 10 and 33% of the amino acids of the GXY part of said recombinant collagen-like peptide are proline.

* * * * *